United States Patent
Severin et al.

(10) Patent No.: US 6,488,665 B1
(45) Date of Patent: *Dec. 3, 2002

(54) ANTIMICROBIAL ALCOHOL GEL PRE-OPERATIVE SKIN-PREPARATION DELIVERY SYSTEM

(75) Inventors: Jane E. Severin, Wonder Lake; David K. Jeng, Lombard, both of IL (US); Bruce H. Wilson, Madison, CT (US); David A. Childers, Huntington, WV (US)

(73) Assignee: Allegiance Corporation, McGaw Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/096,256

(22) Filed: Jun. 11, 1998

Related U.S. Application Data

(63) Continuation-in-part of application No. 08/838,308, filed on Apr. 8, 1997, now Pat. No. 5,916,882.

(51) Int. Cl.⁷ .............................................. A61M 5/24
(52) U.S. Cl. .................... 604/200; 604/19; 604/289; 604/310; 401/205; 401/132
(58) Field of Search .......................... 604/19, 200, 310, 604/289, 309; 141/110; D4/137, 199; 15/34; D24/114; 427/429; 222/212, 215; 239/327; 401/132–135, 205–207

(56) References Cited

U.S. PATENT DOCUMENTS

| 4,057,624 A | 11/1977 | Hase et al. |
| RE29,656 E | 6/1978 | Chittenden et al. |
| 4,128,634 A | 12/1978 | Hase et al. |

(List continued on next page.)

OTHER PUBLICATIONS

Huang et al. American Journal of Infection Control. vol. 22(4): 224–227, 1994*

Journal: AM. J. Infect. Control, Huang Y.; Oie S.; Kamiya A., Comparative effectiveness of hand–cleansing agents for removing methicillin–resistant *Staphylococcus aureus* from experimentally contaminated fingertips, 1994, pp. 3–4.

*Primary Examiner*—Wynn Wood Coggins
*Assistant Examiner*—Jennifer Maynard
(74) *Attorney, Agent, or Firm*—Andrew G. Rozycki; Donald O. Nickey

(57) ABSTRACT

The present invention provides antimicrobial skin-preparation delivery systems useable to disinfect a surgical site for surgery. The delivery systems include an antimicrobial alcohol gel formulation contained within a sealed, flexible container and a gel formulation dispenser connected to the container. The gel formulation dispenser includes a container connector connected to the flexible container and a gel applicator having a sealed piercing member which is slidably engaged with the container connector. An applicator pad is porous and also has enlarged holes for passage of the gel formulation. The gel formulation dispenser pierces a seal in the container and delivers the antimicrobial alcohol gel formulation from the container to the surgical site. Flow rate of the gel formulation is largely controlled by the amount of external pressure of squeezing a user applied to the flexible container. The antimicrobial skin-preparation formula includes iodine, alcohol and gel.

15 Claims, 8 Drawing Sheets

U.S. PATENT DOCUMENTS

| | | | |
|---|---|---|---|
| 4,155,663 A | * 5/1979 | Cerquozzi | 401/135 |
| 4,234,103 A | 11/1980 | Strobl, Jr. et al. | |
| 4,374,126 A | 2/1983 | Cardarelli et al. | |
| 4,415,288 A | * 11/1983 | Gordon et al. | 401/132 |
| 4,498,796 A | 2/1985 | Gordon et al. | |
| 4,507,111 A | 3/1985 | Gordon et al. | |
| 4,542,012 A | 9/1985 | Dell | |
| 4,584,192 A | 4/1986 | Dell et al. | |
| 4,898,293 A | 2/1990 | Morel | |
| 4,925,327 A | * 5/1990 | Wirt | 401/205 |
| 4,976,379 A | 12/1990 | Sloan | |
| 4,978,527 A | 12/1990 | Brink et al. | |
| 5,013,763 A | 5/1991 | Tubesing et al. | |
| 5,042,690 A | 8/1991 | O'Meara | |
| 5,071,648 A | 12/1991 | Rosenblatt | |
| 5,089,606 A | 2/1992 | Cole et al. | |
| 5,118,508 A | 6/1992 | Kikuchi et al. | |
| 5,120,301 A | 6/1992 | Wu | |
| 5,137,718 A | * 8/1992 | Gillespie | 424/78.24 |
| 5,173,291 A | 12/1992 | Brink et al. | |
| 5,288,159 A | 2/1994 | Wirt | |
| 5,288,493 A | 2/1994 | Martino et al. | |
| 5,376,366 A | * 12/1994 | Petchul et al. | 424/78.07 |
| 5,446,070 A | 8/1995 | Mantelle | |
| 5,508,024 A | 4/1996 | Tranner | |
| 5,547,662 A | 8/1996 | Khan et al. | |
| 5,597,561 A | 1/1997 | Kross | |
| 5,607,699 A | 3/1997 | Hoang et al. | |
| 5,629,006 A | 5/1997 | Hoang et al. | |
| 5,674,513 A | 10/1997 | Synder, Jr. et al. | |
| 5,713,843 A | 2/1998 | Vangness | |
| 5,763,412 A | 6/1998 | Khan et al. | |
| 5,769,552 A | 6/1998 | Kelley et al. | |
| 5,916,882 A | 6/1999 | Jeng | |
| 5,922,314 A | 7/1999 | Hoang et al. | |

* cited by examiner

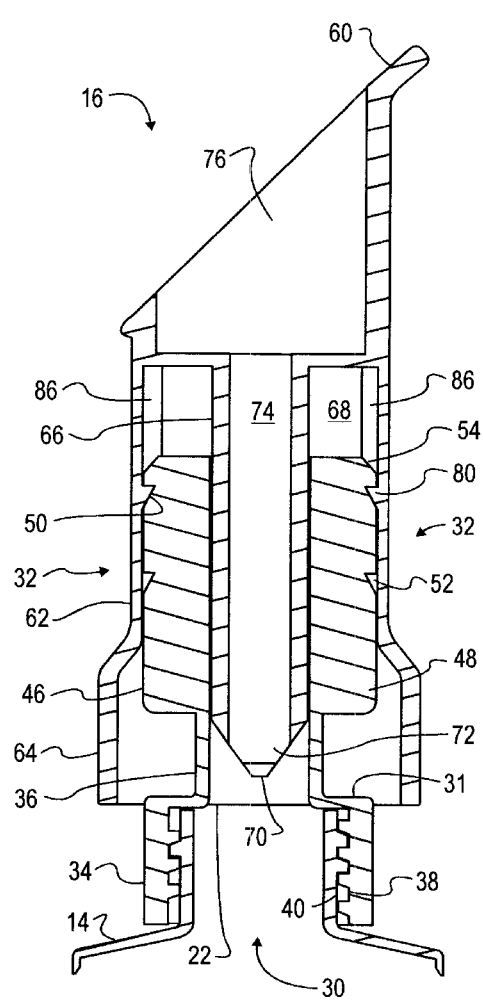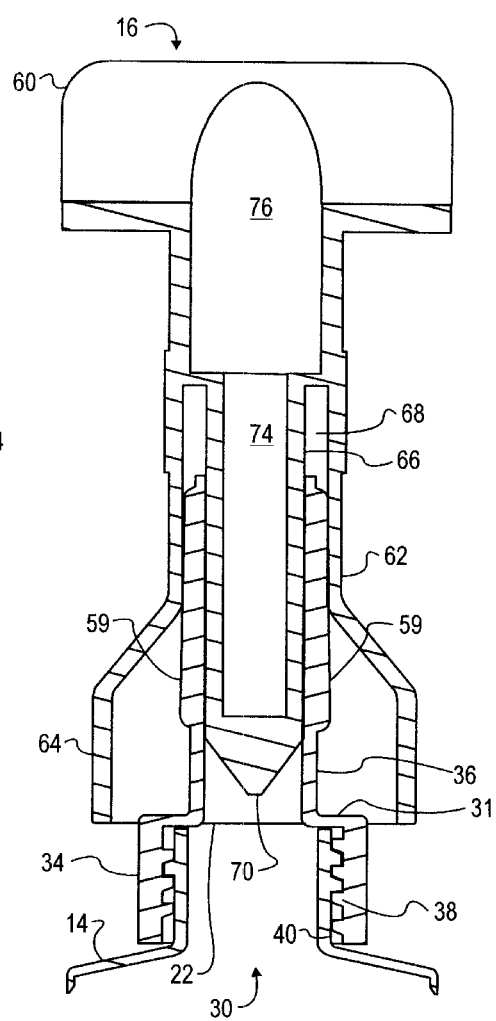

FIG. 4
FIG. 5
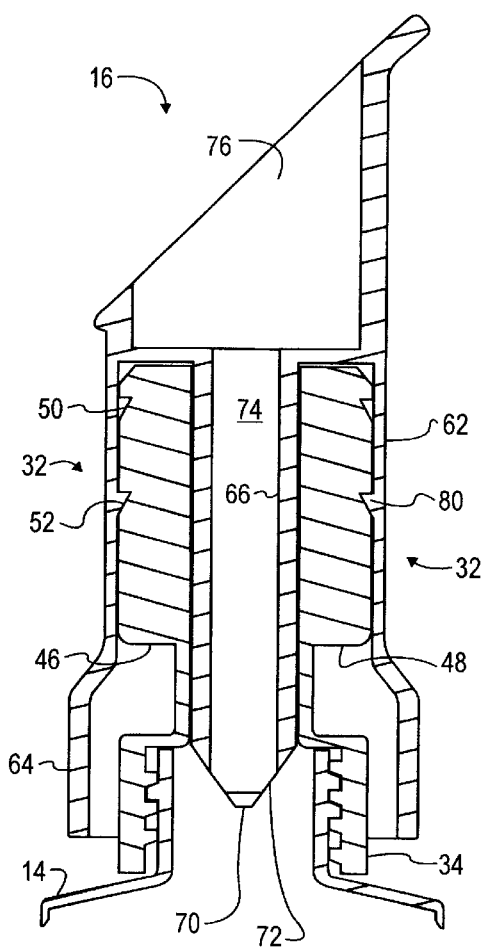
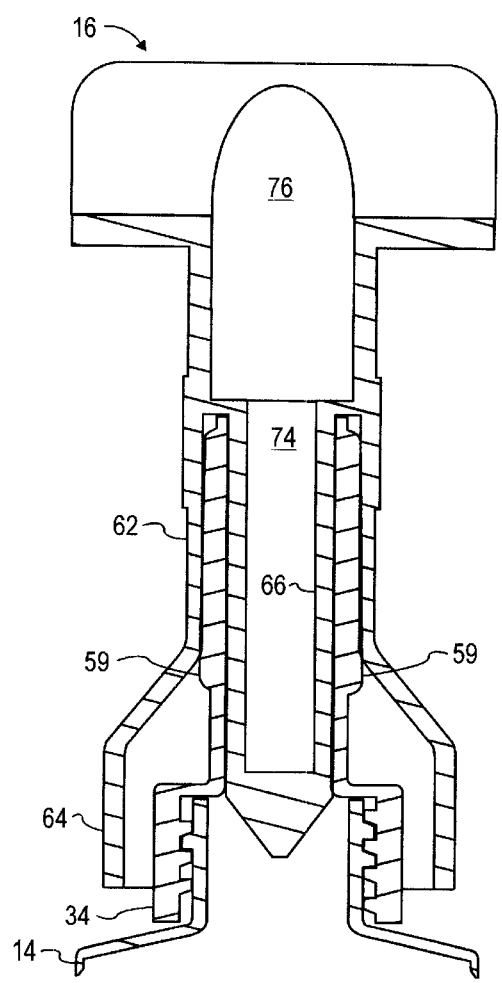

ANTIMICROBIAL ALCOHOL GEL PRE-OPERATIVE SKIN-PREPARATION DELIVERY SYSTEM

RELATED APPLICATION DATA

This application is a continuation-in-part of U.S. Ser. No. 08/838,308, filed Apr. 8, 1998, now U.S. Pat. No. 5,916,882.

FIELD OF THE INVENTION

The present invention generally relates to antimicrobial pre-operative skin-preparation delivery systems and more specifically, the present invention relates to antimicrobial, such as povidone iodine (PVP-I), alcohol pre-operative antimicrobial skin-prepataions in a gel form and delivery devices for the skin-preparations.

BACKGROUND OF THE INVENTION

Standard surgical procedures require the surgical site to be disinfected prior to surgery. Effective pre-operative cleansing of the surgical site is critical to reducing the risk of infection to the patient. Pre-operative skin preparation is therefore as important as the prophylactic antibiotic treatment in control of infection.

Microorganisms on the skin can be transient or resident. Transient microorganisms lie on the surface of the skin, while resident microorganisms are found at deeper sites in the skin, for example, in skin hair follicles. During pre-operative procedures it is desirable to initially kill the microorganisms relatively quickly to reduce the length of time to prepare the patient for surgery. It is also important that the antimicrobial activity can be sustained throughout the surgical procedure by the skin-preparation.

Iodophore has been widely used as a disinfectant and as a pre-operative skin preparation. Pre-operative skin-preparation liquid solutions such as PVP-I scrub and paint solutions are commonly used to disinfect the surgical site prior to surgery. Liquid pre-operative skin-preparations have been stored in liquid containers and dispensed from the liquid containers for application to the surgical site. Existing iodophore skin-preparation solutions typically include iodine, surfactant and a buffer system to provide appropriate pH in an aqueous system. The solutions typically contain an active ingredient of 7.5% to 10.0% povidone iodine. These concentrations of iodine are desirable to provide effective and extended killing of microorganisms.

The conventional method of application of a skin-preparation is to pour bottled skin scrub (7.5% PVP-I) onto a tray, dip a dry sponge into the skin-preparation and apply the soaked sponge to the surface of skin. The skin-preparation is applied from the center to the peripheral areas of the skin site with a circular motion for two to five (2–5) minutes. The sponge provides a physical force to spread the skin-preparation evenly and to remove dead skin cells and skin debris to help the delivery of the skin-preparation to the exposed bacteria. The site is then blotted dry and a skin-preparation paint (10% PVP-I) is applied to the site for two (2) minutes. Conventional skin-preparation systems include several parts and are rather cumbersome to handle. An improved skin-preparation delivery system which does not require the conventional multi-step operation and which requires a shorter time of application is highly desirable and will improve the efficiency and reduce waste.

One existing skin-preparation applicator includes a rigid plastic outer bottle and an applicator head having a sponge. A breakable glass ampule is contained within the rigid plastic bottle. The sealed glass ampule contains a liquid skin-preparation prior to use. The applicator is used by fracturing the glass ampule which releases the liquid skin-preparation. The applicator is tilted to point the applicator head downward such that the liquid skin-preparation travels from the fractured glass ampule to the applicator head. Flow control of the liquid skin-preparation is obtained by varying the amount of tilt of the applicator, and also to some degree, the sponge on the head of the applicator controls the liquid flow rate. A filter screen is provided at the applicator head to trap broken glass from the fractured ampule.

Aqueous iodophore skin-preparations tend to run on the patient's body to areas that don't require disinfection, for example, between the patient and the operating table, and may accumulate on those undesired areas where the iodine can cause skin irritation in certain patients. Gel has been added to povidone iodine to reduce running of the skin-preparation. It provides a film texture allowing the antimicrobial to localize at the desirable surgical incision site without reducing the thickness of iodine from the site. Typically, the iodine content of the gel form is about 10.0% w/v or the effect of antimicrobial activity would not be prominent. Povidone iodine containing gel has been stored in containers; however, such containers have not been designed for holding and effectively delivering the povidone iodine gel to a surgical site. In addition, it is desirable if the applicator can be designed such that the skin-preparation flow rate can be controlled to prevent free flow, particularly for liquid skin-preparations.

Although iodine gel provides the advantage as described, it kills microorganisms at a relative slower rate than other antimicrobial agents such as alcohol. Alcohol has long been recognized as a disinfectant which reduces bacteria, fungi, and some viruses at a great speed. However, alcohol alone evaporate quickly. The disinfection action of alcohol does not continue once the alcohol evaporates from the skin. Accordingly, alcohol alone lacks the prolonged ability to disinfect the surgical site.

Various existing containers have been used to store and dispense liquid products, for example, liquid products such as skin-preparation solutions. However, such liquid containers have not been designed for safely storing and effectively delivering antimicrobial alcohol gel skin-preparations. It is desirable to protect pre-operative skin-preparations from contamination while being stored in a container. Also, liquid dispensers typically restrict the flow of the liquid to reduce excessive or uncontrolled dispensing of the liquid. Such liquid dispensers may not adequately protect or provide adequate flow of gels because of the container structure and the different flow characteristics of gels compared to liquids. Furthermore, some existing containers and dispensers have relatively complex constructions which may require numerous components that can result in increased manufacturing costs.

The present invention beneficially provides antimicrobial gel skin-preparation delivery systems which hold and dispense antimicrobial alcohol gel skin-preparations. The delivery systems are capable of being manufactured and shipped with the skin-preparation protectively sealed within a flexible container while providing quick and easy penetration of the seal to open the container for delivery of the skin-preparation.

The present invention by adding alcohol to iodine gel provides further benefits of a rapid and sustained antimicrobial activity, localization of skin preparation by forming a film on the skin, and a single-step of shortened time period application. The invention also provides an opportunity to lower iodine concentration requirement thus reducing the incidence of irritation of certain patients. All these characteristics, in combination, are not described in the precedent skin-preparations or storage and delivery systems.

SUMMARY OF THE INVENTION

The present invention provides antimicrobial alcohol gel pre-operative skin-preparation delivery systems for storing and delivering skin-preparations. The skin-preparation delivery systems are easily, efficiently and cost effectively manufacturable and reliably store and deliver antimicrobial alcohol gel formulations. The antimicrobial alcohol gel formulation is protectively sealed within a flexible container until use of the formulation is desired. A gel formulation dispenser is activated to allow delivery of the antimicrobial alcohol gel formulation from the container to a desired site.

The opening to the container is induction sealed with an aluminum foil seal which provides a gas impermeable seal. The gel formulation dispenser has a shoulder hat abuts the sealed edge of the container. The shoulder provides additional integrity nd tightness to the seal between the aluminum foil and the edge of the opening to the container. The gel formulation dispenser has a hollowed spike which can be used to activate the delivery system by sliding the spike toward the seal of the container. The spike can be slid toward the seal by pressing the gel formulation dispenser and the container towards each other. The spike is situated in a non-activated position before use and punctures the aluminum foil seal when placed in activated position which then allows the iodine alcohol gel formulation to flow through the hollowed cavity of the spike. The formulation flows from the hollow spike to an angled sponge head for application to the patient. The angled sponge has openings or holes and is ergonomically designed for skin contact. The ergonomically designed sponge effectively contacts and conforms to contours and folds of the skin. Typically, the sponge is used against the targeted skin area and scrubs the skin from the center to the peripheral areas in a circular movement. The total extractable of the sponge of the dispenser is within the limit of medical devices. The flow rate of the iodine alcohol gel formulation is controlled by the amount of pressure squeezed onto the container by the user's hand, because the container has flexible walls. The container itself forms a handle of the delivery system and is sufficiently far enough away from the skin to avoid direct touch to the skin by the gloved hand holding the delivery system.

The gel formulation dispenser is connected to the container and has two separate and distinct locked positions, non-activated and activated positions. The formulation dispenser insures that the delivery system is maintained in the non-activated position until activated by a user and also contributes to a single use nature of the system. The skin-preparation delivery system is a single use system because the formulation dispenser cannot be returned to the non-activated position after activation under normal use. Also, the gel formulation dispenser reduces or eliminates accidental opening of the container because the gel formulation dispenser must be manually moved from the non-activated position to the activated position.

The volume of the new skin-preparation delivery system can be easily varied by using different sized containers. Different surgical procedures may require differing amounts of the skin-preparation. By varying the size of the container, the skin-preparation delivery system can be customized for particular surgical procedures. This can reduce waste of skin-preparation use by avoiding oversized delivery systems. Use of multiple delivery systems for a single surgical procedure can also be avoided by customizing the size of the container for the procedure. Accordingly, the present invention can be customized to provide the desired amount of skin-preparation for one or more specific surgical procedures.

Once the skin-preparation delivery system is placed in the activated position, the gel formulation dispenser defines a gel delivery pathway. The gel delivery pathway through the gel formulation dispenser is designed according to the flow characteristics of the antimicrobial alcohol gel formulation such that a desired flow rate of the formulation is achieved. For example, the desired flow rate of the antimicrobial alcohol gel formulation may be a flow rate which quickly and easily delivers the viscous gel formulation from the container to the desired site. Preferably, the antimicrobial alcohol gel formulation is a PVP-I alcohol gel formulation; however, other viscous or non-viscous antimicrobial formulations may be used with the new delivery systems.

The present invention also provides iodine alcohol gel antimicrobial skin-preparations useable to disinfect a surgical site for surgery. The new pre-operative skin-preparation quickly and effectively kills microorganisms when applied to the surgical site. The skin-preparation continues to effectively inhibit microorganism growth in the applied area for a relatively long period of time. Application of the skin-preparation is highly controllable because it does not easily run when applied to a patient. The antimicrobial skin-preparation meets or exceeds the Food and Drug Administration's proposed performance requirement for pre-operative skin-preparations.

The antimicrobial skin-preparation formula includes iodine, alcohol and gel. The concentration of iodine is relatively low compared to existing skin-preparations. However, the new skin-preparation kills microorganisms quickly upon initial application to the skin and continues to kill microorganisms over an extended period of time. The skin-preparation includes an alcohol at 60.0%–90.0% v/v, an iodophor (iodine) at 1.0%–15.0% w/v, and a gel at 0.1%–20.0% w/v. A preferred antimicrobial skin-preparation includes ethanol at 62.0% v/v, povidone iodine at 5.0% w/v, and gel at 7.5% w/v. Other active and enhancing substances such as surfactants can also be included in the formula.

One advantage of the present invention is that it provides new iodine alcohol gel antimicrobial pre-operative skin-preparation delivery systems which efficiently and effectively store and deliver antimicrobial alcohol gel formulations.

Another advantage of the present invention is to provide skin-preparation delivery systems which can be customized to deliver a desire amount of skin-preparation for a particular surgical procedure.

Another advantage of the present invention is to provide skin-preparation delivery systems which reduce or eliminate contamination of the formulations yet provide quick and easy activation of the system for delivery of the formulations.

Another advantage of the present invention is to provide skin-preparation delivery systems having gel formulation dispensers which are designed for delivery of antimicrobial alcohol gel formulations.

Another advantage of the present invention is to provide povidone iodine alcohol gel antimicrobial pre-operative skin-preparation delivery systems which are easy to use, cost efficient to manufacture, an reliably store and deliver antimicrobial alcohol gel formulations.

Another advantage of the present invention is to provide single use skin-preparation delivery systems.

Another advantage of the present invention is to provide skin-preparation delivery systems which have no glass components.

Another advantage of the present invention is to provide skin-preparation delivery systems which provide improved flow control of the delivery of iodine alcohol gel formulations.

Another advantage of the present invention is to provide skin-preparation delivery systems having a flexible container which contains an iodine alcohol gel formulation.

Another advantage of the present invention is to provide antimicrobial alcohol gel formulations which are easily removed after surgery.

Other objects and advantages of the present invention will become apparent upon reading this disclosure including the appended claims with reference to the accompanying drawings.

BRIEF DESCRIPTION OF THE DRAWINGS

FIG. 2 is a cross-sectional view of the skin-preparation delivery system of FIG. 1 showing the system in a non-activated position.

FIG. 3 is another cross-sectional view of the skin-preparation delivery system. of FIG. 1 also showing the system in a non-activated position.

FIG. 4 is a cross-sectional view of the skin-preparation delivery system of FIG. 1 showing the system in an activated position.

FIG. 5 is another cross-sectional view of the skin-preparation delivery system of FIG. 1 also showing the system in an activated position.

DETAILED DESCRIPTION OF PRESENTLY PREFERRED EMBODIMENTS

Although the present invention can be made in many different forms, the presently preferred embodiments are described in this disclosure and shown in the attached drawings. This disclosure exemplifies the principles of the present invention and does not limit the broad aspects of the invention only to the illustrated embodiments.

The new pre-operative skin-preparation delivery systems of the present invention have an antimicrobial alcohol gel formulation contained within a container and a gel formulation dispenser attached to the container. The antimicrobial alcohol gel formulation provides the pre-operative skin-preparation of the surgical site. The container and the gel formulation dispenser provide a device for storing and delivering the antimicrobial alcohol gel formulation to the surgical site in a desired, effective manner. The formulation, container and dispenser cooperate together to form a new delivery system for pre-operative skin-preparation.

Figure 1:
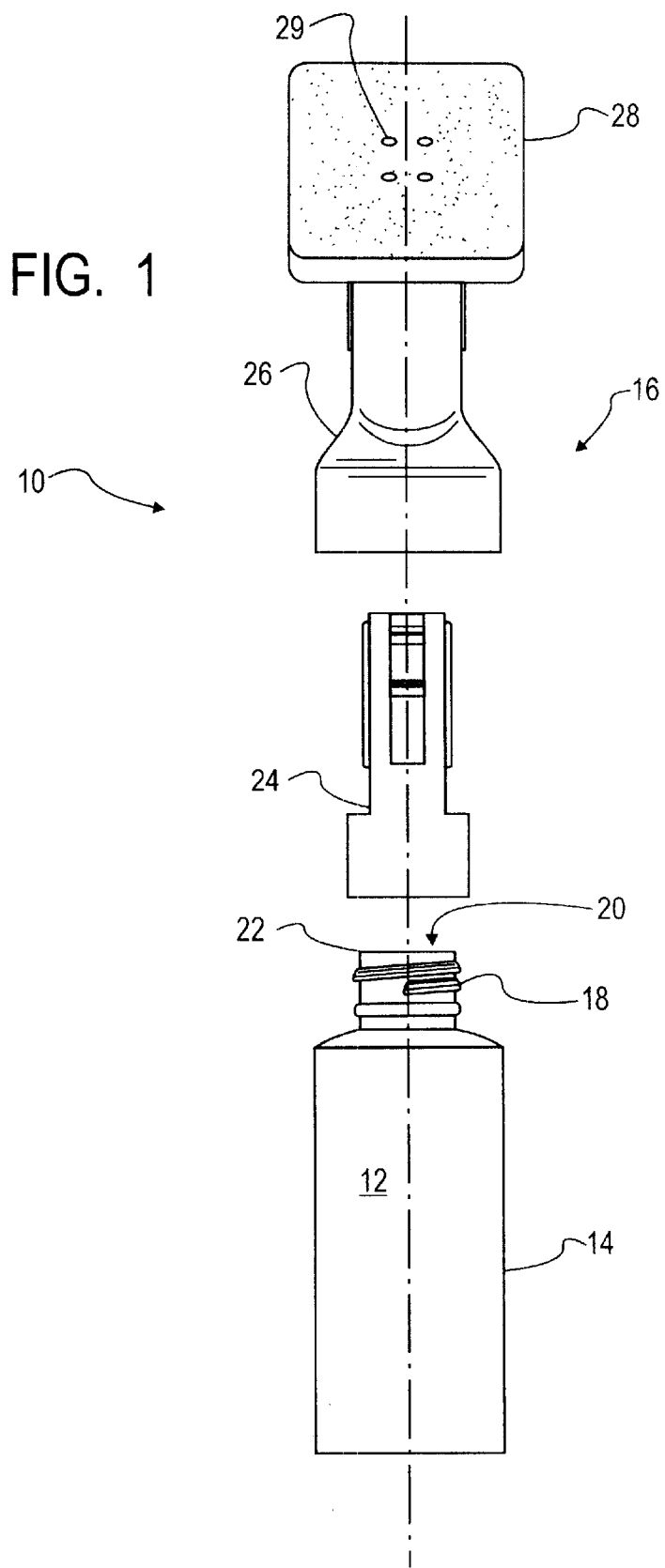
FIG. 1 is an exploded view of an antimicrobial alcohol gel pre-operative skin-preparation delivery system according to the principles of the present invention.
Figure 6:
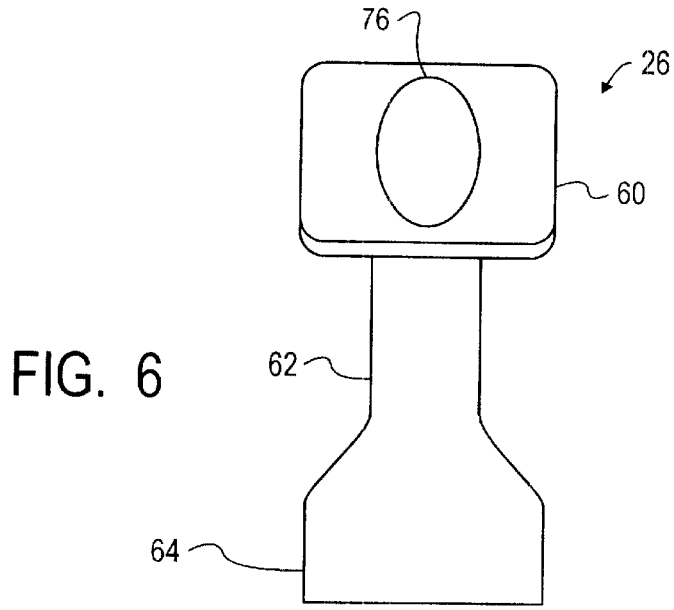
FIG. 6 is an elevational view of a gel applicator of the skin-preparation delivery system of FIG. 1.
Figure 7:
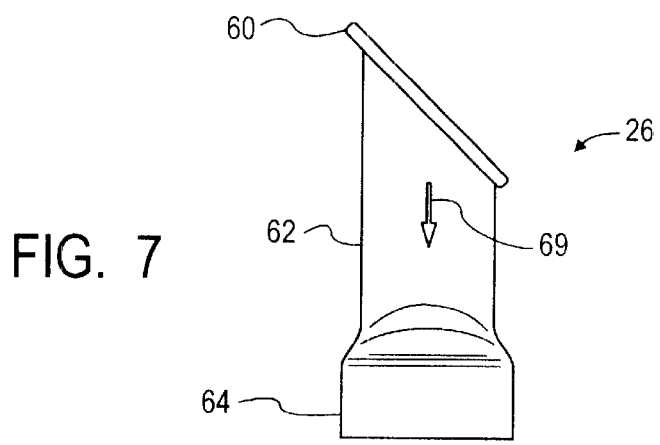
FIG. 7 is a side elevational view of the gel applicator of FIG. 6.
Figure 8:
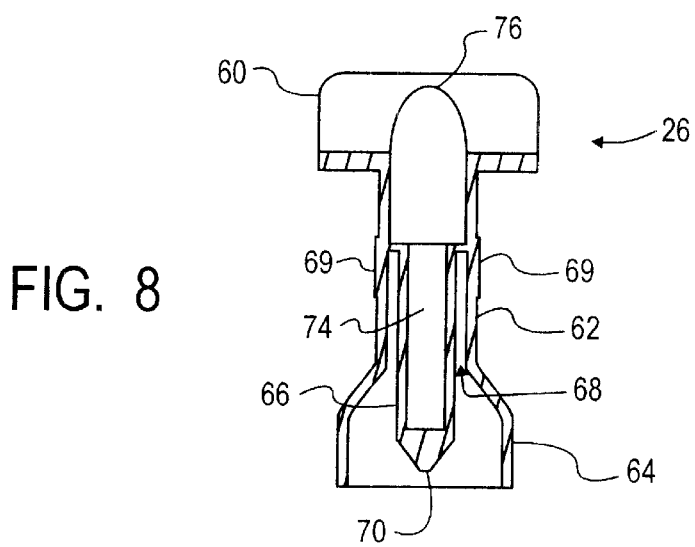
FIG. 8 is a cross-sectional view of the gel applicator of FIG. 6.

One new PVP-I alcohol gel antimicrobial pre-operative skin-preparation delivery system 10 is shown by way of example in FIG. 1. The delivery system 10 includes an antimicrobial alcohol gel formulation 12 contained within a container 14, and a gel formulation dispenser 16 connected tom the container 14. A neck 18 is provided at one end of the container 14 and defines a container opening 20. A seal 22 seals the container opening 20 to maintain the antimicrobial alcohol gel formulation 12 inside of the container 14. The gel formulation dispenser 16 includes a container connector 24 connected to the container 14 and gel applicator 26 engaged with the container connector 24. The container connector 24 and the gel applicator 26 cooperate to pierce the seal 22 and allow the antimicrobial alcohol gel formulation 12 to pass from the container 14 through the formulation dispenser 16 for application to a surgical site. The gel applicator 26 includes a gel applicator pad or sponge 28 for applying the antimicrobial alcohol gel formulation 12 to the surgical site.

The applicator pad 28 is permanently attached to the gel applicator 26 at an angled position relative to a longitudinal axis of the gel applicator 26. Holes 29 are provided in the gel applicator pad 28 to assist in delivering the antimicrobial alcohol gel formulation 12 to the surgical site and to assist ion flow control of the formulation. Accordingly, the antimicrobial alcohol gel formulation 12 passes through the sponge-like applicator pad 28 and also through the holes 29 in the applicator pad 28. The gel applicator pad 28 has a soft texture for comfort when contacting the skin and is suitable for topical medical use.

The container 14 may be formed of any desired flexible material and may have any desired size and shape. For example, the container 14 may be formed from a material suitable for medical applications and may have a generally cylindrical shape. The container 14 may be resiliently flexible such that the container 14 can be squeezed to dispense the antimicrobial alcohol gel formulation 12 from the skin-preparation delivery system 10.

The seal 22 seals the antimicrobial alcohol gel formulation 12 within the container 14; thus, the seal 22 protects the antimicrobial alcohol gel formulation 12 from becoming contaminated. The seal 22 is pierceable such that the seal 22 can be penetrated to allow delivery of the antimicrobial alcohol gel formulation 12 from the container 14. Preferably, the seal 22 is a frangible seal such that when the seal 22 is pierced, the seal 22 is permanently broken. The frangible seal 22 contributes to making the skin-preparation delivery system 10 a single use delivery system because the frangible seal 22 cannot be resealed once broken.

Referring to FIGS. 2 and 3, the skin-preparation delivery system 10 is shown in a non-activated position. In the non-activated position of the skin-preparation delivery system 10, a seal piercing member 30 on the gel formulation dispenser 16 is spaced away from the seal 22 on the container 14. Because the seal piercing member 30 is spaced away from the seal 22 in the non-activated position, the antimicrobial alcohol gel formulation 12 remains sealed within the container 14. The container connector 24 has a shoulder 31 which abuts the peripheral edge of the seal 22 and assists in maintaining the seal with the container 14. Referring to FIGS. 4 and 5, the skin-preparation delivery system 10 is shown in an activated position. In the activated position of the skin-preparation delivery system 10, the seal piercing member 30 of the gel formulation dispenser 16 is pierced through the seal 22. Accordingly, the antimicrobial alcohol gel formulation 12 can be dispensed from the container 14 and delivered to a desired location from the skin-preparation delivery system 10.

Referring to FIGS. 2–5, the gel applicator 26 is slidably engaged with the container connector 24 and is slidably movable from the non-activated position to the activated position. A lock 32 is provided on the gel formulation dispenser 16 to maintain the gel formulation dispenser 16 in one of the non-activated and activated positions. The lock 32 maintains the gel applicator 26 in the non-activated position until a user actuates the gel applicator 26 by sliding the gel applicator 26 toward the container 14 to the activated position in which the seal 22 is pierced by the seal piercing member 30. Once the gel applicator 26 has been moved to the activated position, the lock 32 locks the gel applicator 26 in the activated position. Accordingly, the gel applicator 26 is prevented from sliding away from the container 14 by the lock 32 when the gel applicator 26 is in either the non-activated or activated positions. In this manner, the lock 32 contributes to the single use feature of the skin-preparation delivery system 10.

Referring to FIGS. 2, 3 and 12–14, the container connector 24 has a connection end 34 and an elongated tube 36 extending from the connection end 34. The gel formulation dispenser 16 is connected to the container 14 by the connection end 34 of the container connector 24. The connection end 34 may have threads 38 which are engaged with threads 40 on the neck 18 of the container 14 to removably connect the gel formulation dispenser 16 to the container 14. The gel formulation dispenser 16 could also be permanently connected to the container 24. The elongated tube 36 defines a passageway 42 through the container connector 24. The passageway 42 receives a portion of the gel applicator 26 and may have a substantially uniform diameter along its length. The elongated tube 36 and the connection end 34 may be coaxially aligned along an axis of the container connector 24.

A lock portion 44 of the lock 32 is provided on the elongated tube 36. The lock portion 44 has wings 46, 48 on diametrically opposed sides of the elongated tube 36. Upper and lower recesses 50, 52 are provided on each of the wings 46, 48. An upper slanted surface 54 is provided on each wing 46, 48 which permits easy assembly of the gel applicator 26 to the container connector 24. A perpendicular surface 56 defines part of the upper recess 50 to prevent removal of the gel applicator 26 from the container connector 24 when the gel formulation dispenser 16 is in the non-activated position. Slanted surfaces 57 also define a part of the upper recesses 50 and permit the gel applicator 26 to slide to the activated position. The lower recess 52 is also defined by a perpendicular surface 58 which prevents the gel applicator 26 from sliding on the container connector 24 away from the container 14 after the gel formulation dispenser 16 is positioned in the activated position.

Rails 59 projecting from the outside of the elongated tube 36 may be provided to stabilize the sliding of the container connector 24 in the gel applicator 26.

Referring to FIGS. 2, 3 and 6–11, the gel applicator 26 includes a gel applicator head 60 extending from one end of an outer tube section 62 and an expanded apron 64 extending from an opposite end of the outer tube section 62. An elongated gel dispensing tube 66 is positioned inside of the outer tube section 62 and the expanded apron 64 such that a channel 68 is defined between the gel dispensing tube 66 and the outer tube section 62. The gel dispensing tube 66 is connected to the gel applicator head 60 and extends towards the expanded apron 64. The elongated tube 36 of the container connector 24 slides within the channel 68 and thus, the gel applicator 26 and the container connector 24 are engaged together. In this manner, the gel applicator 26 telescopically moves relative to the container connector 24 because the elongated tube 36 is received by the channel 68. Downward pointing arrows 69 may be provided on the gel applicator 26 to indicate the direction of movement of the gel applicator 26 on the container connector 24.

The seal piercing member 30 is provided at a lower end of the gel dispensing tube 66. The seal piercing member 30 has a seal piercing point 70 and a plurality of gel formulation pathways 72 adjacent the seal piercing point 70. A gel formulation pathway 74 is defined inside of the gel dispensing tube 66 and an enlarged gel formulation pathway 76 is defined through the gel applicator head 60. The gel formulation pathway 72 through the seal piercing member 30, the gel formulation pathway 74 through the gel dispensing tube 66 and the enlarged gel formulation pathway 76 through the gel applicator head 60 cooperate together to define the gel flow pathway from the container 14 through the gel formulation dispenser 16. The gel formulation pathways 72, 74, 76 may be sized and shaped to correspond with the flow characteristics of the antimicrobial alcohol gel formulation such that a desired flow rate of the formulation through the skin-preparation delivery system is achieved. The desired flow rate of the antimicrobial alcohol gel formulation is an appropriate flow rate for applying a skin-preparation to a patient. The gel pathway 74 through the gel dispensing tube 66 is shown as having a substantially uniform diameter along its length and extending along a majority of a length of the gel passageway through the gel formulation dispenser 16.

The gel applicator pad 28 having the holes 29 and the amount of pressure squeezed onto the flexible container 14 provide the flow control of the antimicrobial alcohol gel formulation through the delivery system 10. The container connector 24 and the gel applicator 26 of the gel formulation dispenser 16 tend to provide little restriction to the flow of the antimicrobial alcohol gel formulation compared to the gel applicator pad 28. The density of the gel applicator pad 28 and the size of the holes 29 in the pad affect the flow of the antimicrobial alcohol gel formulation. The seal 22 on the container 14 may cover a portion of the gel formulation pathway 72 in the seal piercing member 30 when the seal piercing point 70 pierces the seal 22. However, the seal 22 tends to move off of the gel formulation pathway 72 in the seal piercing member 30 when pressure is applied to the flexible container 14.

A lock portion 78 of the lock 32 is provided on an inside surface of the outer tube section 62. The lock portion 78 includes a pair of projections 80 on opposite sides of the outer tube section 62. Each projection 80 has an upper perpendicular surface 82 and a lower slanted surface 84. The lower slanted surfaces 84 slide over the upper slanted surfaces 54 of the wings 46, 48 on the container connector 24 to assemble the container connector 24 and the gel applicator 26 together. The upper perpendicular surfaces 82 of the projections 80 on the gel applicator 26 cooperate with the perpendicular surfaces 56 on the upper recesses 50 of the wings 46, 48 to prevent removal of the gel applicator 26 from the container connector 24. The projections 80 on the lock portions 78 of the gel applicator 26 extend into the upper recesses 50 on the container connector 24 when the gel formulation dispenser 16 is in the non-activated position. The upper perpendicular surfaces 82 and the lower slanted surfaces 84 of the projections 80 cooperate with the slanted surfaces 57 of the upper recesses 50 and the perpendicular surfaces 58 of the lower recesses 52 on the container connector 24 to permit the gel formulation dispenser 16 to move from the non-activated position to the activated position and to prevent the gel formulation dispenser 16 from moving from the activated position back to the non-activated position.

The gel applicator head 60 may be positioned at an angel relative to a central, longitudinal axis of the gel applicator 26 to assist in effectively applying the antimicrobial alcohol gel formulation to a desired location.

Figure 9:
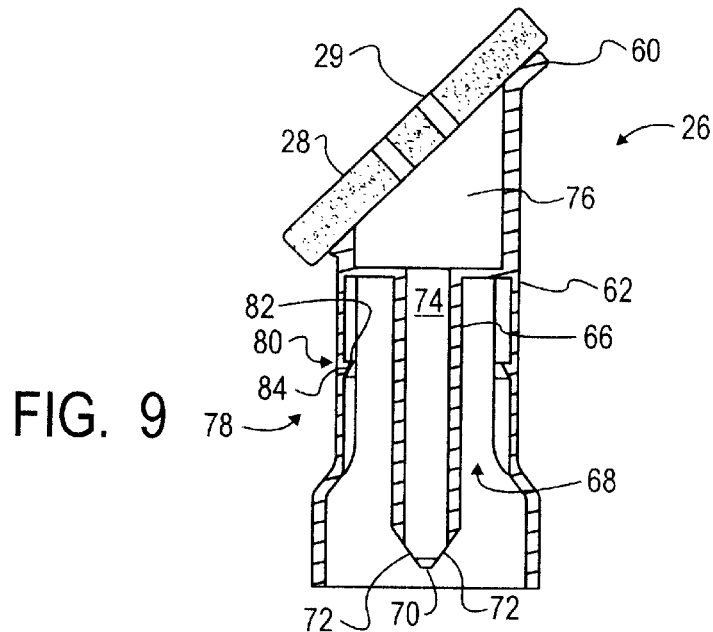
FIG. 9 is another cross-sectional view of the gel applicator of FIG. 6.
Figure 10:
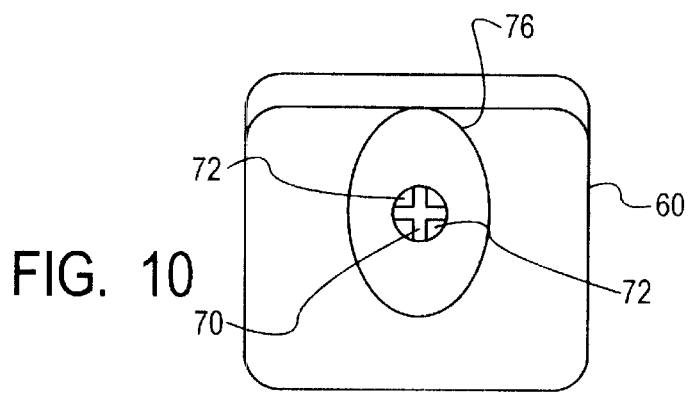
FIG. 10 is a top end view of the gel applicator of FIG. 6.
Figure 11:
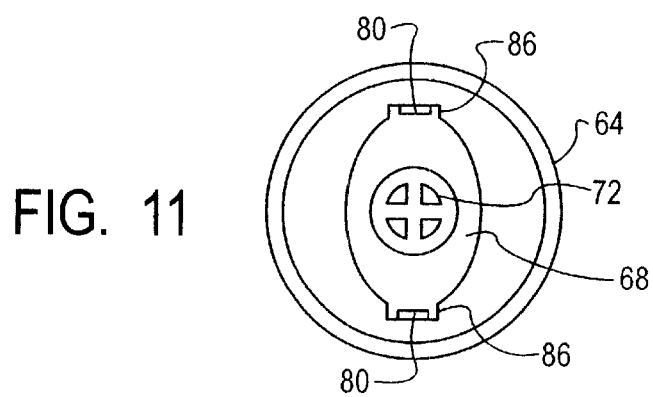
FIG. 11 is a bottom end view of the gel applicator of FIG. 6.
Figure 12:
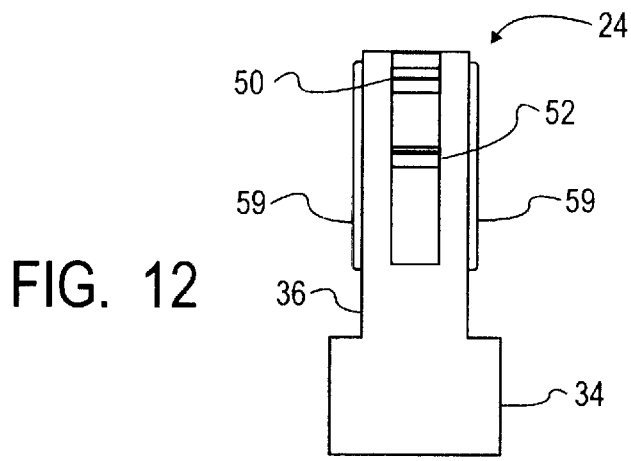
FIG. 12 is an elevational view of a container connector of the skin-preparation delivery system of FIG. 1.
Figure 13:
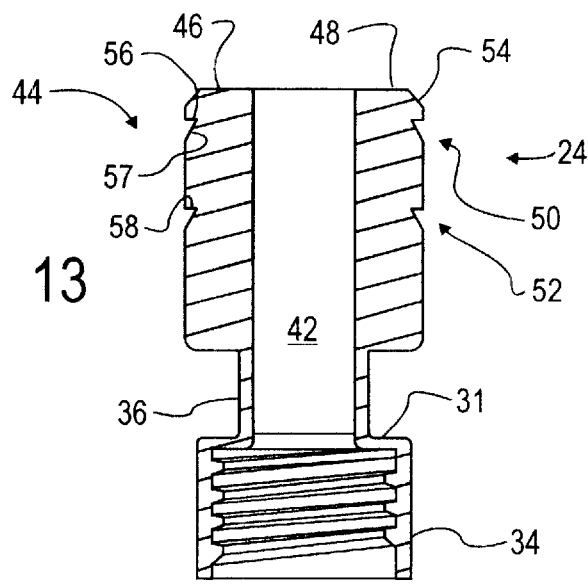
FIG. 13 is a cross-sectional view of the container connector of FIG. 12.
Figure 14:
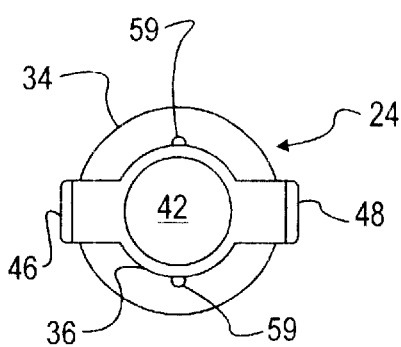
FIG. 14 is a top end view of the container connector of FIG. 12.
Figure 15:
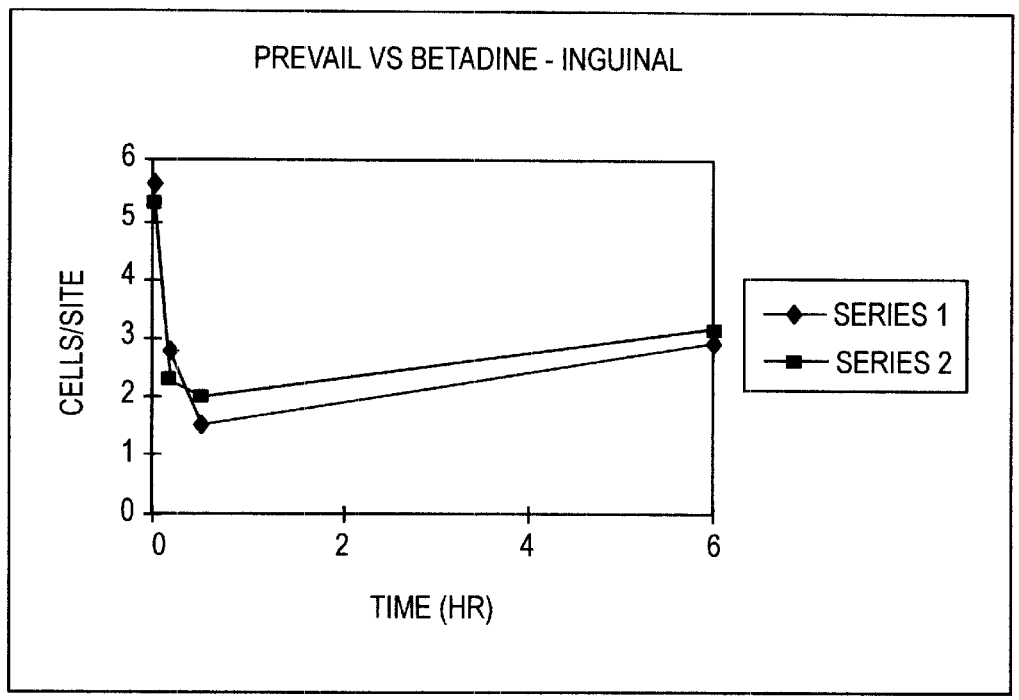
FIG. 15 is a graph showing antimicrobial activity of the present invention PVP-I alcohol gel skin-preparation on normal flora of human inguinal site as described in Example II.
Figure 16:
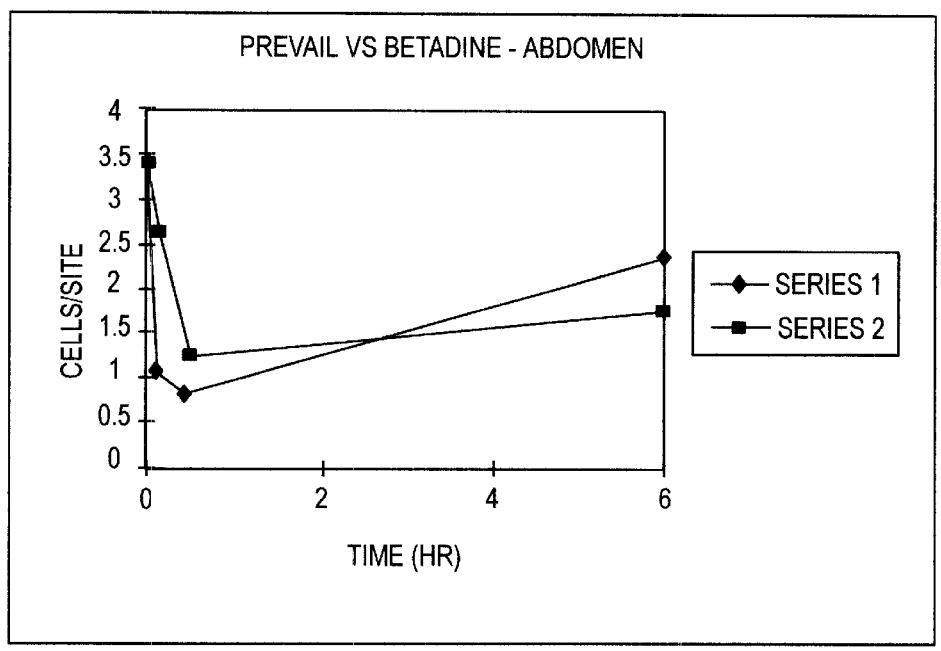
FIG. 16 is a graph showing antimicrobial activity of the present invention PVP-I alcohol gel skin-preparation on normal flora of human skin abdomen site as described in Example II.

Referring to FIGS. 9 and 11, the gel applicator 26 includes a pair of diametrically opposed slide channels 86 extending along the outer tube section 62. The wings 46, 48 of the container connector 24 are received in and slide along the slide channels 86. The slide channels 86 and the wings 46, 48 also maintain the gel applicator 26 at a constant rotational position relative to the container connector 24, i.e., the gel applicator 26 is prevented from rotating relative to the container connector 24. The projections 80 of the lock portions 78 on the gel applicator 26 are positioned within the slide channels 86. The rails 59 on the container connector may contact the inside of the outer tube section 62 of the gel applicator 26 and assist in stabilizing the device.

The new pre-operative antimicrobial skin-preparation 12 of the delivery system 10 has a formulation of alcohol, iodine, and gel. The skin-preparation provides rapid and prolonged antimicrobial action. Both transient and resident microorganisms are effectively controlled by the skin-preparation. The skin-preparation is intended to be used for surgery but may also be used for other appropriate applications, for example as a surgical hand wash and general disinfectant. The antimicrobial skin-preparation generally includes alcohol, iodine and gel. The combination of these components provides an initial rapid kill of the microorganisms, a prolonged kill of the resident microorganisms over an extended period of time, and maintains the skin-preparation at the desired localized surgical site to provide a continuous antimicrobial activity at an effective iodine concentration level if not washed off. Because of the initial rapid kill of the microorganisms, only a short amount of time is required to apply the skin-preparation to the patient. The skin-preparation is also relatively mild and minimizes skin irritation. The skin-preparation is easily and effectively applied to a desired location, such as a surgical site, by the gel formulation dispenser 16.

A presently preferred antimicrobial skin-preparation in accordance with the present invention includes the following components:

| alcohol | 60.0%–90.0% v/v |
|---------|-----------------|
| iodine  | 1.0%–15.0% w/v  |
| gel     | 0.1%–30.0% w/v  |

A carrier solvent may be included in the formula to make up 100% of the volume. Other optional components may also be included, for example:

| base pH adjuster       | 0.01%–2.0% w/v |
|------------------------|----------------|
| acid pH adjuster       | 0.01%–5.0% w/v |
| skin irritation reducer| 0.1%–5.0% w/v  |

One antimicrobial skin-preparation which has been found to be effective includes the following components:

| ethyl alcohol   | 60.0%–90.0% v/v |
|-----------------|-----------------|
| povidone iodine | 1.0%–15.0% w/v  |
| gel             | 0.1%–20.0% w/v  |

A carrier solvent and other optional components may also be included, for example:

| sodium hydroxide | 01%–2.0% w/v   |
| citric acid      | 0.01%–5.0% w/v |
| glycerin         | 0.1%–5.0% w/v  |

One presently preferred formulation of the antimicrobial skin-preparation includes the following components:

| ethyl alcohol   | 62.0% v/v |
| povidone iodine | 5.0% w/v  |
| gel             | 7.5% w/v  |

Optional components may be included, for example:

| sodium hydroxide | 0.2% w/v |
| citric acid      | 0.5% w/v |
| glycerin         | 1.0% w/v |

The antimicrobial skin-preparation includes an alcohol as one of the components. The alcohol provides a rapid and effective initial kill of microorganisms. Alcohol rapidly reduces microbial counts once the preparation is applied to the skin and leads iodine to the deeper site of the skin for effective control of resident microorganisms. Alcohols which are suitable for use in health care applications to human skin can be used in the skin-preparation. For example, suitable alcohols include ethyl alcohol, methyl alcohol, isopropyl alcohol, butyl alcohol, propyl alcohol, and other similar alcohols including phenyl alcohol. The concentration of alcohol included in the skin-preparation is selected to provide a rapid, effective initial control of the microorganisms while not being too high to cause instability in the formulation, such as breaking down the gel. Preferably, the amount of alcohol included in the skin-preparation is about 60.0%–90.0% v/v. One presently preferred formulation of the skin-preparation includes ethyl alcohol at about 62.0% v/v.

The antimicrobial skin-preparation includes iodine as one of the components. The iodine provides an effective continued kill of microorganisms. Iodine continues to reduce microbial counts and inhibits microorganisms from growing and repopulating the surgical site. The iodine in the skin-preparation also effectively controls both transient and resident skin inhabiting microorganisms. Preferable iodines for use in the skin-preparation are iodophores (complexes of iodine), and specifically, povidone iodine (PVP-I). Povidone iodine is typically available in a solid powder form and is soluble in an aqueous condition or in a water-alcohol mix. The concentration of povidone iodine in the formulation is selected to provide effective microorganism control over an extended period of time. Preferably, the amount of povidone iodine included in the skin-preparation is about 1.0%–15.0% w/v. One presently preferred formulation of the skin-preparation can have a significantly less concentration of iodine than the concentration in existing pre-operative iodine based skin-preparations, which typically include 7.5%–10.0% w/v iodine. The present inventive skin-preparation surprisingly provides enhanced microorganism control even at relatively lower iodine concentrations. The effective control of microorganisms, both initially and through an extended period, is due to the combination of alcohol, iodine, and gel.

The antimicrobial skin-preparation also includes a gel as one of the components. The gel provides a medium for applying the skin-preparation to the surgical site. The gel gives the skin-preparation a syrup-like consistency and assists in maintaining the microorganism killing agents at the surgical site. The gel formulation reduces running of the skin-preparation by forming a film on the skin and thus, delivers the disinfection action more effectively to the desired skin location. Accordingly, the skin-preparation tends to remain localized at the surgical site where the disinfecting action is needed. The concentration of the iodine can be reduced because the initial action of alcohol enables the skin-preparation to have a lower concentration of iodine in inhibiting the growth of the resident microorganisms. The lower concentration of iodine contributes to less skin irritation.

The gel also reduces the potential for exposing other skin areas on the patient to the skin-preparation. Preferable gels for use in the skin-preparation are water soluble and compatible with the particular alcohol and iodine used in the formulation. The concentration of gel in the formulation is selected to increase the viscosity of the skin-preparation and provide the ability of maintaining the skin-preparation at or close to the desired location on the patient as a film. Preferably, the amount of gel included in the skin-preparation is about 0.1%–20.0% w/v. One preferred formulation of the skin-preparation includes gel at about 7.5% w/v. A preferred gel includes simethicone hydroxypropylcellulose and nonoxynol-10. The simethicone may be included at about 0.1%–20% w/v of the sin-preparation, for example 5.0% w/v of the skin-preparation. The hydroxypropylcellulose may be included at about 0.1%–30% w/v of the skin preparation, for example 2.0% w/v of the skin-preparation. The nonoxynol-10 may be included at about 0.1%–15% w/v of the skin preparation, for example 0.5% w/v of the skin-preparation. Hydrogels may also be suitable for use in the skin-preparation.

The antimicrobial skin-preparation may also include a carrier solvent as one of the components. The carrier solvent provides the balance of the formulation to make 100% of the volume. A suitable carrier solvents are compatible with the particular alcohol, iodine, and gel components in the skin-preparation. The preferable carrier solvent is sterile water.

The antimicrobial skin-preparation formulation may include other components. Acid and base adjusters may be added to maintain a proper pH level. Base pH adjusters can include for example, alkali metal hydroxides. Suitable alkali metal hydroxides include sodium hydroxide and potassium hydroxide, for example. On preferred skin-preparation includes sodium hydroxide at about 0.01%–2.0% w/v of the skin-preparation, and preferably, 0.2% w/v. Acid pH adjusters can include various acid, such as citric acid, lactic acid and acetic acid, for example. One preferred skin-preparation includes citric acid at about 0.01%–5.0% w/v of the skin-preparation, and preferably, 0.5% w/v. The skin-preparation may include skin irritation reducers to reduce the potential for irritating the patient's skin. Suitable skin irritation reducers include glycerin, petroleum jelly, petrolatum, mineral oil, ethylene glycol, and glycerol, for example. One preferred skin-preparation includes glycerin at about 0.1%–5.0% w/v of the skin-preparation, and preferably, 1.0% w/v.

Additional components can also be added to the skin-preparation as desired. For example, a dye could be added to provide a desired color. Fatty acids could be added to lengthen the time of antimicrobial action for an even longer term of protection. Surfactants could also be added to create lather, for example, when the formulation is used as a hand wash.

The antimicrobial gel skin-preparation has been tested and found to be effective at rapidly killing microorganisms and inhibiting growth of microorganisms by maintaining its killing action for an extended period of time. The federal Food and Drug Administration ("FDA") has published proposed test methods and performance requirements for healthcare disinfectants, including skin-preparations. The FDA's proposed methods and performance requirements are described in the Tentative Final Monograph for Health-Care Antiseptic Drug Products (the "TFM"). The present antimicrobial skin-preparing has been subjected to the TFM Time-Kill test and Minimum Inhibition Concentration test as discussed in Example I. The present antimicrobial skin-preparation has also been subjected to the TFM efficacy test to evaluate the antimicrobial activity on human skin normal flora for both transient and resident microorganisms using inguinal and abdomen skin testing sites. The skin-preparation meets or exceeds the TFM requirements. Various existing skin-preparation solutions were also tested according to the TFM requirements for comparison to the present gel skin-preparation invention. The gel skin-preparation of the present invention exhibited antimicrobial control equal to or better than the existing solutions.

By way of example, and not limitation, examples of the present invention will now be given. The tests in these examples were performed according to the FDA test protocols and thus, the new delivery system 10 was not used during the tests.

EXAMPLE I

In Vitro Time-Kill Test and Minimum Inhibition Concentration Test in Evaluation of AntiMicrobial Efficacy An antimicrobial gel skin-preparation according to the present invention was tested for antimicrobial efficacy with the challenge bacteria listed in the FDA's TFM. In addition, the gel skin-preparation was also tested against other bacteria of clinical importance with resistance to various antibiotics. A total of 32 species of microorganisms were used in the tests. Two TFM test methods were conducted in the evaluation of antimicrobial efficacy of the new skin-preparation, specifically, the Time-Kill test and the Minimum Inhibition Concentration test. The skin-preparation contained PVP-I 5% w/v, Ethanol 62% v/v, and gel 7.5% w/v. A control formulation of PVP-I 7.5% w/v, referred to in this example as Betadine, was also tested to provide a comparison to the Prevail skin-preparation.

Principle

It is important that skin-preparations constitute rapid and prolonged antimicrobial action. The Time-Kill test evaluates the rapidity of the antimicrobial action whereas the Minimum Inhibition Concentration assesses the prolonged inhibiting action. The rapidity of the antimicrobial action of the PVP-I alcohol gel skin-preparation was assessed in comparison with the Betadine iodophor control using 15 and 30 seconds of contact in the Time-Kill test. The Minimum Inhibition Concentration test was also conducted to evaluate the long term effectiveness at killing microorganisms. By formulating the PVP-I alcohol gel skin-preparation with PVP-I, alcohol and gel, the antimicrobial action of iodine and alcohol may have synergies or complement each other because of their individual modes of action. The alcohol in the PVP-I alcohol gel formulation enables the antimicrobial skin-preparation to effectively deliver a rapid action against the microorganisms tested and enables the amount of PVP-I to be reduced from a conventional amount of 10% w/v to 5% w/v in the present invention. A lower PVP-I tends to reduce skin irritation caused by the iodophor in certain patients.

Purpose

To comparatively determine the antimicrobial efficacy of PVP-I alcohol gel skin-preparation and a iodophor control (Betadine) in a 15 and 30 seconds Time-Kill test and a Minimum Inhibition Concentration test.

Materials and Methods

A. Samples
1. PVP-I alcohol gel skin-preparation (PVP-I 5% w/v, ethanol 62% v/v, gel 7.5% w/v) 4 oz bottle.
2. Control: Betadine PVP-I 7.5% v/v.

B. Methods
1. Time-Kill test: A 1 ml of bacterial culture containing approximately $10^9$/ml bacterial counts was added into 9 ml of the testing products (PVP-I alcohol gel skin-preparation and Betadine control) and mixed vigorously. Samples were taken and transferred to neutralization solution after 15 seconds and 30 seconds exposures. The 15 second and 30 second exposure samples were bioassayed for survival microorganisms by a pour plate method.
2. Minimum Inhibition Concentration test: Equivalent volumes of each of the bacterial cultures was added into each of the testing products (PVP-I alcohol gel skin-preparation and Betadine control) and a series of 1:2 dilution of the mix was made with sterile saline. The mixed materials were incubated for 48 hours to observe the microbial growth.

Results

A. Time-Kill Test: Table 1 shows that the present invention PVP-I alcohol gel skin-preparation is efficacious to reduce at least 5 log, in 15 seconds, for all testing organisms including those aerobic, anaerobic bacteria and yeasts as proposed by the TFM. The log reduction represents the amount of the organisms killed during the 15 second or 30 second time periods, i.e., the greater the log reduction the greater amount of the organism that was killed. PVP-I alcohol gel skin-preparation is also efficacious to reduce the antibiotic resistant organisms with clinical significance. The PVP-I alcohol gel skin-preparation exhibited superior control in antimicrobial activity to the control, particularly with the trend to better control of antibiotic resistant bacterial species.

B. Minimum Inhibition Concentration Test: Table 2 shows that the present invention PVP-I alcohol gel skin-preparation produced similar antimicrobial inhibition activity to the iodophor Betadine control. The concentrations shown in Table 2 represent the minimum concentrations of the PVP-I alcohol gel skin-preparation and the control that limit microbial growth to a TFM specified amount over a 48 hour period.

TABLE 1

Comparative study of PVP-I alcohol gel and iodophor control in microbial Time-Kill test of the organisms listed in the TFM and other antibiotic resistant species in a 15 second and a 30 second exposures.

| | LOG REDUCTION | | | |
| --- | --- | --- | --- | --- |
| | 15 sec | | 30 sec | |
| | PVP-I alcohol gel | Control* | PVP-I alcohol gel | Control* |
| Staphylococcus aureus (ATCC #6538) | >8.63 | 7.32 | >8.63 | >8.63 |
| Staphylococcus aureus (ATCC #29213) | >5.94 | >5.94 | >5.94 | >5.94 |
| Staphylococcus aureus (ATCC #33591) M,V** | >6.07 | 2.11 | >6.07 | 4.27 |
| Staphylococcus aureus (ATCC #33592) G,M** | >6.15 | 2.24 | >6.15 | >6.15 |
| Staphylococcus aureus (ATCC #33593) G,M** | >5.71 | >5.71 | >5.71 | >5.71 |
| Staphylococcus aureus (ATCC #33594) G** | >6.03 | >6.03 | >6.03 | >6.03 |
| Staphylococcus aureus (ATCC #43300) M** | >5.78 | 2.90 | >5.78 | >5.78 |
| Staphylococcus epidermidis (ATCC #12228) | >5.40 | >5.40 | >5.40 | >5.40 |
| Staphylococcus epidermidis (ATCC #51624) M** | >5.75 | 2.86 | 5.40 | 2.89 |
| Staphylococcus epidermidis (ATCC #51625) M** | >5.33 | >5.33 | >5.33 | >5.33 |
| Staphylococcus haemolyticus (ATCC #29970) | >5.13 | 2.15 | >5.13 | >5.13 |
| Staphylococcus hominis (ATCC #25615) | >5.22 | 1.79 | >5.22 | >5.22 |
| Staphylococcus saprophyticus (ATCC #15305) | >5.55 | 2.26 | >5.55 | >5.55 |
| Streptococcus pyogenes (ATCC #12351) | >4.51 | >4.51 | >4.51 | >4.51 |
| Streptococcus pneumoniae (ATCC #35088) | >4.37 | 3.06 | >4.37 | >4.37 |
| Micrococcus lureus (ATCC #7468) | >4.56 | >4.56 | >4.56 | >4.56 |
| Enterococcus faecalis (ATCC #29212) | >5.98 | >5.98 | >5.98 | >5.98 |
| Enterococcus faecalis (ATCC #51575) G,S,V** | >6.04 | 4.63 | >6.04 | >6.04 |
| Enterococcus faecium (ATCC #49224) | >5.61 | 3.84 | >5.61 | 4.97 |
| Acinetobacter anitratus (ATCC #49137) | >5.42 | >5.42 | >5.42 | >5.42 |
| Enterobacter cloacae (ATCC #13047) | >5.98 | >5.98 | >5.98 | >5.98 |
| Eschericia coli (ATCC #11229) | >7.66 | >7.66 | >7.66 | >7.66 |
| Eschericia coli (ATCC #25922) | >5.82 | >5.82 | >5.82 | >5.82 |
| Klebsiella pneumoniae (ATCC #27736) | >5.58 | 4.02 | >5.58 | >5.58 |
| Klebsiella oxytoca (ATCC #15764) | >5.70 | >5.70 | >5.70 | >5.70 |
| Proteus mirabilis (ATCC #4630) | >6.11 | >6.11 | >6.11 | >6.11 |
| Pseudomonas aeruginosa (ATCC #15442) | >6.02 | >6.02 | >6.02 | >6.02 |
| Pseudomonas aeruginosa (ATCC #27853) | >5.81 | >5.81 | >5.81 | >5.81 |
| Serratia marcescens (ATCC #14756) | >5.95 | >5.95 | >5.95 | >5.95 |
| Bacteroides fragilis | >5.54 | 4.81 | >5.54 | >5.54 |

TABLE 1-continued

Comparative study of PVP-I alcohol gel and iodophor control in microbial Time-Kill test of the organisms listed in the TFM and other antibiotic resistant species in a 15 second and a 30 second exposures.

| | LOG REDUCTION | | | |
|---|---|---|---|---|
| | 15 sec | | 30 sec | |
| | PVP-I alcohol gel | Control* | PVP-I alcohol gel | Control* |
| (ATCC #25285) Cadida albicans (ATCC #10231) | >7.58 | 2.04 | >7.58 | 5.00 |
| Candida tropicalis (ATCC #750) | 3.23 | 1.82 | >5.54 | 3.35 |

*Betadine PVP-I (7.5%).
**Resistance in: M = Methicillin; G = Gentamicin; S = Streptomycin; V = Vancomycin

TABLE 2

Comparative study of PVP-I alcohol gel and iodophor control in Minimum Inhibition Concentration test with the organisms listed in the TFM and other antibiotic resistant species.

| | Minimum Inhibition Concentration* | |
|---|---|---|
| | PVP-I alcohol gel | Control** |
| Staphylococcus aureus (ATCC #6538) | 1:128 | 1:32 |
| Staphylococcus aureus (ATCC #29213) | 1:32 | 1:32 |
| Staphylococcus aureus (ATCC #33591) M,V*** | 1:64 | 1:64 |
| Staphylococcus aureus (ATCC #33592) G,M*** | 1:128 | 1:32 |
| Staphylococcus aureus (ATCC #33593) G,M*** | 1:64 | 1:64 |
| Staphylococcus aureus (ATCC #33594) G*** | 1:64 | 1:64 |
| Staphylococcus aureus (ATCC #43300) M*** | 1:64 | 1:64 |
| Staphylococcus epidermidis (ATCC #12228) | 1:64 | 1:64 |
| Staphylococcus epidermidis (ATCC #51624) M*** | 1:32 | 1:32 |
| Staphylococcus epidermidis (ATCC #51625) M*** | 1:64 | 1:64 |
| Staphylococcus haemolyticus (ATCC #29970) | 1:64 | 1:64 |
| Staphylococcus hominis (ATCC #25615) | 1:128 | 1:32 |
| Staphylococcus saprophyticus (ATCC #15305) | 1:128 | 1:32 |
| Streptococcus pyogenes (ATCC #12351) | 1:32 | 1:16 |
| Streptococcus pneumoniae (ATCC #35088) | 1:64 | 1:128 |
| Micrococcus lureus (ATCC #7468) | 1:32 | 1:32 |
| Enterococcus faecalis (ATCC #29212) | 1:32 | 1:32 |
| Enterococcus faecalis (ATCC #51575) G,S,V*** | 1:32 | 1:32 |
| Enterococcus faecium (ATCC #49224) | 1:64 | 1:32 |
| Acinetobacter anitratus (ATCC #49137) | 1:16 | 1:32 |
| Enterobacter cloacae (ATCC #13047) | 1:16 | 1:32 |
| Eschericia coli (ATCC #11229) | 1:16 | 1:32 |
| Eschericia coli (ATCC #25922) | 1:64 | 1:32 |
| Klebsiella pneumoniae (ATCC #27736) | 1:16 | 1:32 |
| Klebsiella oxytoca (ATCC #15764) | 1:16 | 1:32 |
| Proteus mirabilis (ATCC #4630) | 1:32 | 1:32 |
| Pseudomonas aeruginosa (ATCC #15442) | 1:32 | 1:32 |
| Pseudomonas aeruginosa (ATCC #27853) | 1:32 | 1:16 |
| Serratia marcescens (ATCC #14756) | 1:16 | 1:32 |
| Bacteroides fragilis (ATCC #25285) | 1:32 | 1:16 |
| Cadida albicans (ATCC #10231) | 1:64 | 1:32 |
| Candida tropicalis (ATCC #750) | 1:16 | 1:32 |

*Dilution from the original concentration.
**Betadine PVP-I (7.5%).
***Resistance in: M = Methicillin; G = Gentamicin; S = Streptomycin; V = Vancomycin

EXAMPLE II

Clinical Antimicrobial Efficacy Determination on Normal Flora of Human Skin

An antimicrobial gel skin-preparation according to the present invention was also tested for antimicrobial efficacy on normal flora of human skin as specified in the FDA's TFM. The new PVP-I alcohol gel skin-preparation formulation was subjected to a vigorous efficacy test to evaluate the antimicrobial activity on human skin normal flora for both transient and resident microorganisms using inguinal and abdomen skin testing sites. The PVP-I alcohol gel skin-preparation contained PVP-I 5% w/v, Ethanol 62% v/v, and gel 7.5% w/v. A control formulation of PVP-I 10.0% w/v, referred to in this example as Betadine, was also tested to provide a comparison to the PVP-I alcohol gel skin-preparation.

Principle

The TFM proposes that the efficacy is measured on human inguinal and abdomen skin sites for the reduction of normal microbial flora. Ten minutes after the application, a minimum of three-log reduction from a baseline of at least $10^5$ cells per site in inguinal area and a two-log reduction from a baseline of at least $10^3$ cells per site in abdomen area are required. The survival organisms shall not grow to greater than the baseline level in 6 hours after the application. The action of the new PVP-I alcohol gel skin-preparation and the comparison formulations were evaluated in single applications of 30 seconds. The Betadine control was tested at a 5 minute application.

Purpose

To comparatively determine the antimicrobial efficacy in a 30-second-one-time application of the present invention versus a 5 minute application of a traditional Betadine iodophor solution control.

Materials

A. Samples
  1. PVP-I alcohol gel skin-preparation (PVP-I 5% w/v, ethanol 62% v/v, gel) 4 oz bottle.

2. Control: Betadine PVP-I 10% v/v solution (iodophor solution).

B. Subjects

1. Number: Twelve (12) randomly selected human volunteers of both sexes.
2. Age: Between 18 to 70 with healthy skin.
3. Subjects were pre-screened to exhibit a microbial baseline of $10^5$ and $10^3$ organisms per inguinal and abdomen testing site, respectively.

Protocol

A. Before Treatment

1. A two-week wash off time is assigned to subjects without the use of products containing antimicrobial agents.
2. A baseline sample is taken from randomized testing sites with stripping solution containing neutralizer according to the method described in the TFM.
3. The present invention PVP-I alcohol gel formulation is applied onto test sites, scrubbing in a circular motion with a sponge for 30 seconds or 1 minute. The control Betadine solution is similarly applied for 5 minutes and replenished when dry.

B. After Treatment

1. At 10 minutes, 30 minutes and 6 hours post-application, samples were taken from randomized test sites according to the method described in the TFM using a striping solution containing an appropriate neutralizer.
2. Samples were assayed for survival colonies by the agar pour plate method.

Results

Tables 3 and 4 show that the present invention PVP-I alcohol gel skin-preparation in a 30 second one step application satisfied the requirements specified by the TFM in inguinal (groin) (Table 3) and abdomen (Table 4) testing sites. The new skin-preparation reduced at least 3 logs of normal flora in 10 minutes post-application and the microbial level did not rise to greater than the baseline in 6 hours. The log reduction numbers represent the amount of normal flora killed or reduced below the baseline. Accordingly, a 1 log reduction drop below the baseline indicates a 90% kill, a 2 log reduction drop below the baseline indicates a 99% kill, and a 3 log drop below the baseline indicates a 99.9% kill, etc. FIGS. 1 and 2 graphically show the test results of the performance of the PVP-I alcohol gel formulation and the Betadine control solution. FIG. 1 shows antimicrobial activity of PVP-I alcohol gel skin-preparation vs. Betadine control on normal flora of human inguinal site: Series 1=PVP-I alcohol gel (30 sec application time); Series 2=Betadine control (5 min application time). FIG. 2 shows antimicrobial activity of PVP-I alcohol gel skin-preparation vs. Betadine control on normal flora of human abdomen site: Series 1=PVP-I alcohol gel (30 sec application time); Series 2 Betadine control (5 min application time). As can be seen in Tables 3 and 4, the present invention exhibited superior performance as compared to the 62% ethanol gel and the 5% PVP-I gel alone for both the inguinal and abdomen tests. The PVP-I alcohol gel skin-preparation of the present invention had a greater log reduction (greater microorganism kill) than the other two gels after 10 minutes, 30 minutes and 6 hours.

TABLE 3

Antimicrobial activity of the PVP-I alcohol gel skin-preparation at inguinal site in comparison with ethanol gel and PVP-I gel using Betadine PVP-I (10%) as a control.

| | | | Log Reduction per Inguinal Site | | |
|---|---|---|---|---|---|
| Sample | Time | Baseline | 10 mi | 30 min | 6 hr |
| PVP-I alcohol gel | 30 sec | 5.656 | 2.950 | 4.141 | 2.784 |
| 62% Ethanol Gel | 30 sec | 5.396 | 2.274 | 1.581 | 0.546 |
| 5% PVP-I Gel | 30 sec | 5.396 | 2.272 | 1.372 | 0.686 |
| Betadine | 5 min | 5.339 | 3.053 | 3.352 | 2.247 |

TABLE 4

Antimicrobial activity of the PVP-I alcohol gel skin-preparation at abdomen site in comparison with ethanol gel and PVP-I gel using Betadine PVP-I (10%) as a control.

| | | | Log Reduction per Abdomen Site | | |
|---|---|---|---|---|---|
| Sample | Time | Baseline | 10 min | 30 min | 6 hr |
| PVP-I alcohol gel | 30 sec | 3.748 | 2.692 | 2.937 | 1.393 |
| 62% Ethanol Gel | 30 sec | 3.928 | 1.990 | 1.669 | 0.059 |
| 5% PVP-I Gel | 30 sec | 3.928 | 2.018 | 1.404 | 0.136 |
| Betadine | 5 min | 3.774 | 1.098 | 2.565 | 1.941 |

EXAMPLE III

Example of Making the Present Invention

The presently preferred method of making the PVP-I alcohol gel skin-preparation includes slowly combining the solid PVP-I alcohol gel components with the liquid alcohol. The components are mixed as they are combined. For example, one method of making a 100 ml amount of the skin-preparation will now be described, A test batch of the skin-preparation is made. The desired amounts of PVP-I (e.g., 5.0% w/v), and gel (e.g., 7.5% w/v) are measured and added to a mixing container. Ethyl alcohol is added while mixing until the total volume of 100 ml is obtained. The volume of ethyl alcohol required to make 100 ml of the skin-preparation is noted. Another batch of the skin-preparation is made by placing the amount of alcohol noted in the test batch in a mixing container. The PVP-I and gel components are slowly added to the ethyl alcohol while mixing. The resultant formulation will contain 100 ml of the present invention PVP-I alcohol gel skin-preparation.

The skin-preparation delivery system 10 can be used as follows. The gel applicator 26 and the container connector 24 are assembled together to form the gel formulation dispenser 16. The wings 46, 48 on the container connector 24 are alined with the slide channels 86 on the gel applicator 26. The container connector 24 and gel applicator 26 are slid together until the projections 80 on the gel applicator 26 pass over the upper slanted surfaces 54 on the wings 46, 48 and extend into the upper recesses 50. The container connector 24 and the gel applicator 26 may flex to permit relative sliding of these components. The gel formulation dispenser 16 is now in the non-activated position. If a cap is present on the seal container 14 containing the antimicrobial alcohol gel formulation 12 is present, the cap is removed to expose the neck 18 and the seal 22. The gel formulation dispenser 16 is connected to the container 14 by threaded engagement of a container connector 24 to the neck 18. Alternately, the container connector 24 could be assembled onto the container 14 and then the gel applicator 26 can be assembled onto the container connector 24. The skin-preparation delivery system 10 is now in the non-activated position shown in FIGS. 2 and 3.

The desired area to be treated on the patient is selected. The skin-preparation delivery system 10 is put in the activated position as shown in FIGS. 4 and 5 by sliding the gel applicator 26 on the container connector 24 toward the container 14. The seal piercing member 30 pierces the seal 22 to allow delivery of the antimicrobial alcohol gel formulation 12. The projections 80 on the gel applicator 26 extend into the lower recesses 52 on the wings 46, 48 of the container connector 24 to lock the skin-preparation delivery system into the activated position. The container 14 is squeezed to force the antimicrobial alcohol gel formulation 12 from the container 14 and through the gel formulation dispenser 16 for delivery to a selected area.

The skin-preparation in gel form is applied to the selected area and the area is scrubbed with the skin-preparation. Due to the rapid antimicrobial action of the skin-preparation, the selected area need only be scrubbed for approximately 30 seconds which shortens the amount of time needed for pre-operative procedures. The skin-preparation has been found to be effective in reducing the skin normal flora in 30 seconds. The skin-preparation tends to remain confined to the local area in which it is applied and continues to provide effective killing of microorganisms for an extended period of time. The skin-preparation is water soluble and thus, it is easily cleaned from the patient after surgical operation.

While the presently preferred embodiments have been illustrated and described, numerous changes and modifications can be made without significantly departing from the spirit and scope of this invention. Therefore, the inventor intends that such changes and modifications are covered by the appended claims.

What is claimed is:

1. An antimicrobial gel skin preparation delivery device comprising:

a flexible container having a top opening and including an antimicrobial gel skin preparation composition disposed in the flexible container and a rupturable seal sealing the top opening;

a container connector including a first end releasably connected to the flexible container about the top opening and an elongated hollow tube having an internal passageway extending from the first end to an opposed second end with an opening;

an applicator member including an elongate hollow shaft with a longitudinal bore having a central longitudinal axis, the shaft having a first end with a seal piercing point and at least one opening communicating with the bore and having a second end with a head flange projecting perpendicularly outwardly from the shaft defining an applicator head surface with a central opening communicating with the bore, the applicator head surface being disposed at an angled orientation with respect to the central longitudinal axis;

a sponge applicator having a plurality of gel release holes secured to the applicator head surface so that the gel release holes are disposed adjacent the central opening;

the applicator being engaged with the container connector so that the shaft is telescopically received within the internal passageway; and the container connector and applicator member including cooperatively engageable structural features permitting the applicator member to be moved from an engaged closed position wherein the shaft is received in the internal passageway with the seal piercing point spaced from the rupturable seal and a gel dispensing position wherein the shaft is advanced within the passageway so that the rupturable seal is ruptured by the seal piercing point and antimicrobial gel may flow from the container through the shaft to the sponge applicator, and so that in the gel dispensing position, the applicator member is maintained at a constant rotational position relative to the container connector;

and wherein said antimicrobial gel skin preparation composition comprises alcohol from about 60.0% v/v to about 90.0% v/v of the formulation; iodine from about 1.0% w/v to about 15.0% w/v of the formulation; and gel from about 0.1% w/v to about 20.0% w/v of the formulation.

2. An antimicrobial gel skin preparation delivery device as defined in claim 1, wherein the top opening of the container includes an external threaded section and the first end of the container connector includes internal threads threadedly engaging the external threads.

3. The antimicrobial gel skin-preparation delivery device of claims 1, wherein the applicator member comprises an outer tubular section which defines a channel between the outer tubular section and the elongated tube of the container connector is slideably received in the channel.

4. The antimicrobial gel skin-preparation delivery device of claim 1, wherein the applicator member includes a pair of opposed slide channels and the container connector includes a pair of opposed wings slidably received in the slide channels.

5. The antimicrobial skin-preparation delivery device of claim 1, wherein the alcohol is selected from the group consisting of ethyl alcohol, methyl alcohol, isopropyl alcohol, butyl alcohol and propyl alcohol.

6. The antimicrobial skin-preparation delivery device of claim 1, wherein the iodine is povidone iodine.

7. The antimicrobial skin-preparation delivery device of claim 1, wherein the gel is a water soluble gel.

8. The antimicrobial skin-preparation delivery device of claim 1, wherein the gel comprises:

simethicone from about 0.1% w/v to about 20% w/v of the formulation; and hydroxypropylcellulose from about 0.1% w/v to about 30% w/v of the formulation.

9. The antimicrobial skin-preparation delivery device of claim 1, wherein the antimicrobial gel skin preparation composition further comprises a base pH adjuster from about 0.01% w/v to about 2% w/v of the formulation.

10. The antimicrobial skin-preparation delivery device of claim 9, therein the base pH adjuster is an alkali earth metal hydroxide.

11. The antimicrobial skin-preparation delivery device of claim 1, wherein the antimicrobial gel skin preparation composition further comprises an acid pH adjuster from about 0.01% w/v to about 5% w/v of the formulation.

12. The antimicrobial skin-preparation delivery device of claim 1, wherein the antimicrobial gel skin preparation composition further comprises a skin irritation reducer from about 0.1% w/v to about 5% w/v of the formulation.

13. The antimicrobial skin-preparation delivery device of claim 1, wherein the skin irritation reducer is selected from the group consisting of glycerin, petroleum jelly, petrolatum, mineral oil, ethylene glycol and glycerol.

14. The antimicrobial skin-preparation delivery device of claim 1, wherein the antimicrobial gel skin preparation composition comprises:
  ethyl alcohol at about 62.0% v/v of the formulation;
  povidone iodine at about 5.0% w/v of the formulation; and
  gel at about 7.5% w/v of the formulation.

15. The antimicrobial skin-preparation delivery device of claim 14, wherein the antimicrobial gel skin preparation composition further comprises:
  sodium hydroxide at about 0.2% w/v of the formulation;
  citric acid at about 0.5% w/v of the formulation; and
  glycerin at about 1.0% w/v of the formulation.

* * * * *